United States Patent
DeMan et al.

(10) Patent No.: US 7,639,775 B2
(45) Date of Patent: *Dec. 29, 2009

(54) METHOD AND SYSTEM FOR IMAGING USING MULTIPLE OFFSET X-RAY EMISSION POINTS

(75) Inventors: Bruno DeMan, Clifton Park, NY (US); Peter Michael Edic, Albany, NY (US); Samit Basu, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/970,403

(22) Filed: Jan. 7, 2008

(65) Prior Publication Data
US 2008/0130828 A1 Jun. 5, 2008

Related U.S. Application Data

(63) Continuation of application No. 10/789,539, filed on Feb. 27, 2004, now Pat. No. 7,333,587.

(51) Int. Cl.
*A61B 6/00* (2006.01)
(52) U.S. Cl. ............................................ 378/9; 378/5
(58) Field of Classification Search ............... 378/5, 378/9, 4, 12, 10
See application file for complete search history.

(56) References Cited

U.S. PATENT DOCUMENTS

| | | | |
|---|---|---|---|
| 2,340,500 A | 2/1944 | Zunick et al. | |
| 4,053,779 A * | 10/1977 | Barbieri | 378/9 |
| 4,057,725 A | 11/1977 | Wagner et al. | |
| 4,196,352 A | 4/1980 | Berninger et al. | |
| 4,274,005 A | 6/1981 | Yamamura et al. | |
| 4,284,896 A | 8/1981 | Stonestrom | |
| 4,384,359 A | 5/1983 | Franke | |
| 4,547,892 A | 10/1985 | Richey et al. | |
| 4,637,040 A | 1/1987 | Sohval et al. | |
| 4,947,412 A | 8/1990 | Mattson | |
| 4,965,726 A | 10/1990 | Heuscher et al. | |
| 4,991,190 A | 2/1991 | Mori | |
| 5,166,961 A | 11/1992 | Brunnett | |
| 5,173,852 A | 12/1992 | Lonn | |
| 5,175,754 A | 12/1992 | Casey et al. | |
| 5,228,070 A | 7/1993 | Mattson | |
| 5,259,012 A | 11/1993 | Baker et al. | |
| 5,262,946 A | 11/1993 | Heuscher | |
| 5,276,614 A | 1/1994 | Heuscher | |
| 5,305,363 A | 4/1994 | Burke et al. | |
| 5,335,255 A | 8/1994 | Seppi et al. | |
| 5,377,249 A | 12/1994 | Wiesent et al. | |

(Continued)

*Primary Examiner*—Hoon Song
(74) *Attorney, Agent, or Firm*—Scott J. Asmus

(57) ABSTRACT

A technique is provided for imaging a field of view using an X-ray source comprising two or more emission points. Each emission point is configured to emit a fan of radiation encompassing less than the entire field of view. The emission points are activated individually and rotate about the field of view, allowing respective streams of radiation to be emitted at various view angles about the field of view. The emission points, which may correspond to different radial regions of the field of view, may be differentially activated to emphasize a region of interest within the field of view. The multiple emission points may be extrapolated along the longitudinal axis in duplicate or offset configurations.

18 Claims, 6 Drawing Sheets

U.S. PATENT DOCUMENTS

| | | | |
|---|---|---|---|
| 5,383,231 A | 1/1995 | Yamagishi | |
| 5,396,418 A | 3/1995 | Heuscher | |
| 5,412,562 A | 5/1995 | Nambu et al. | |
| 5,438,605 A | 8/1995 | Burke et al. | |
| 5,485,493 A | 1/1996 | Heuscher et al. | |
| 5,491,734 A | 2/1996 | Boyd et al. | |
| 5,544,212 A | 8/1996 | Heuscher | |
| 5,570,403 A * | 10/1996 | Yamazaki et al. | 378/5 |
| 5,633,906 A | 5/1997 | Hell et al. | |
| 5,654,995 A | 8/1997 | Flohr | |
| 5,719,914 A | 2/1998 | Rand et al. | |
| 5,764,721 A | 6/1998 | Light et al. | |
| 5,848,117 A | 12/1998 | Urchuk et al. | |
| 5,966,422 A | 10/1999 | Dafni et al. | |
| 6,002,738 A | 12/1999 | Cabral et al. | |
| 6,047,040 A | 4/2000 | Hu et al. | |
| 6,125,167 A | 9/2000 | Morgan | |
| 6,130,929 A | 10/2000 | Saha | |
| 6,183,139 B1 | 2/2001 | Solomon et al. | |
| 6,208,711 B1 | 3/2001 | Rand et al. | |
| 6,229,870 B1 | 5/2001 | Morgan | |
| 6,233,308 B1 | 5/2001 | Hsieh et al. | |
| 6,236,705 B1 | 5/2001 | Stergiopoulos et al. | |
| 6,236,709 B1 | 5/2001 | Perry et al. | |
| 6,252,924 B1 | 6/2001 | Davantes et al. | |
| 6,256,369 B1 | 7/2001 | Lai | |
| 6,272,200 B1 | 8/2001 | Pen et al. | |
| 6,333,968 B1 | 12/2001 | Whitlock et al. | |
| 6,353,653 B1 | 3/2002 | Edic | |
| 6,385,280 B1 * | 5/2002 | Bittl et al. | 378/16 |
| 6,385,282 B1 | 5/2002 | Frncke et al. | |
| 6,421,412 B1 * | 7/2002 | Hsieh et al. | 378/9 |
| 6,453,003 B1 | 9/2002 | Springer et al. | |
| 6,459,755 B1 | 10/2002 | Li | |
| 6,466,640 B1 | 10/2002 | Taguchi | |
| 6,507,639 B1 | 1/2003 | Popescu | |
| 6,522,712 B1 | 2/2003 | Yavuz et al. | |
| 6,529,574 B1 | 3/2003 | Hsieh | |
| 6,535,570 B2 | 3/2003 | Stergiopoulos et al. | |
| 6,674,837 B1 | 1/2004 | Taskar et al. | |
| 6,731,716 B2 | 5/2004 | Mihara et al. | |
| 6,754,300 B2 | 6/2004 | Hsieh et al. | |
| 6,760,399 B2 | 7/2004 | Malamud | |
| 6,795,521 B2 | 9/2004 | Hsu et al. | |
| 6,807,248 B2 | 10/2004 | Mihara et al. | |
| 6,879,656 B2 | 4/2005 | Cesmeli et al. | |
| 6,914,959 B2 | 7/2005 | Bailey et al. | |
| 6,934,357 B2 | 8/2005 | Boyd et al. | |
| 7,333,587 B2 * | 2/2008 | De Man et al. | 378/9 |
| 2002/0025017 A1 | 2/2002 | Stergiopoulos et al. | |
| 2002/0074929 A1 | 6/2002 | Taskar et al. | |
| 2002/0085674 A1 | 7/2002 | Price et al. | |
| 2002/0094064 A1 | 7/2002 | Zhou et al. | |
| 2003/0043957 A1 | 3/2003 | Pelc | |
| 2003/0048868 A1 * | 3/2003 | Bailey et al. | 378/65 |
| 2003/0118155 A1 | 6/2003 | Ueno et al. | |
| 2004/0114710 A1 | 6/2004 | Ozaki | |
| 2004/0136490 A1 | 7/2004 | Edic et al. | |
| 2004/0213378 A1 | 10/2004 | Zhou et al. | |
| 2004/0258196 A1 * | 12/2004 | Lounsberry | 378/12 |
| 2005/0089134 A1 | 4/2005 | Bruder et al. | |
| 2005/0135550 A1 | 6/2005 | De Man et al. | |
| 2005/0175143 A1 | 8/2005 | Miyazaki et al. | |
| 2006/0002506 A1 | 1/2006 | Pelc | |

* cited by examiner

METHOD AND SYSTEM FOR IMAGING USING MULTIPLE OFFSET X-RAY EMISSION POINTS

CROSS REFERENCE TO RELATED APPLICATIONS

This application is a Continuation of U.S. patent application Ser. No. 10/789,539, entitled "Method and System for Imaging Using Multiple Offset X-Ray Emission Points", filed Feb. 27, 2004, which is herein incorporated by reference in its entirety for all purposes.

BACKGROUND OF THE INVENTION

The present invention relates generally to the field of non-invasive imaging and more specifically to the field of computed tomography (CT) imaging. In particular, the present invention relates to source configurations useful in CT imaging.

CT scanners operate by projecting fan-shaped or cone-shaped X-ray beams from an X-ray source. The X-ray source emits X-rays at numerous view angle positions about an object being imaged, such as a patient, which attenuates the X-ray beams as they pass through. The attenuated beams are detected by a set of detector elements, which produce signals representing the intensity of the incident X-ray beams. The signals are processed to produce data representing the line integrals of the attenuation coefficients of the object along the X-ray paths. These signals are typically called "projection data" or just "projections". By using reconstruction techniques, such as filtered backprojection, useful images may be formulated from the projections. The images may in turn be associated to form a volume rendering of a region of interest. In a medical context, pathologies or other structures of interest may then be located or identified from the reconstructed images or rendered volume.

It is generally desirable to develop CT scanners with high spatial and temporal resolution, good image quality, and good coverage along the z-axis, i.e., the longitudinal axis of the CT scanner. To meet some or all of these objectives, it may be desirable to increase the coverage provided by the detector, thereby allowing greater scan coverage in one or more dimensions. For example, longitudinal axis coverage of the detector may be improved by increasing the number of rows of detector elements in the detector.

This approach has lead to the development of CT systems with larger detectors. Larger detectors, however, may be undesirable for a variety of reasons. For instance, as one might expect, larger detectors and associated acquisition electronics are both more costly and more difficult to produce. In addition, the mechanical subsystem responsible for supporting and/or rotating a larger detector may also need to be larger and more complex and/or may be subject to greater mechanical stress. Furthermore, large detectors are associated with increased cone angles, i.e., the angle between the source and the detector periphery. The increased cone angle between the source and detector periphery is in turn associated with increased cone-beam artifacts in the reconstructed images. When the cone angle increases beyond a certain limit, the degradation of the image quality may become severe for axial, or step and shoot scanning. For this reason, it may be difficult to increase the scan coverage by simply increasing the coverage, i.e., size of the detector. A technique for achieving high spatial and temporal resolution, good image quality, and good coverage using a standard or smaller detector may therefore be desirable.

BRIEF DESCRIPTION OF THE INVENTION

The present technique provides a novel method and apparatus for providing two or more discrete X-ray emission points, which are laterally offset, i.e., have different xy-coordinates. In particular, the sources are offset in an azimuthal direction such that each source provides a particular subset of the projection lines needed to reconstruct the imaged object within the field of view. The sources may be alternately activated, though not necessarily at equal intervals, i.e., some of the sources may be activated more frequently or for greater duration than others. A single detector may be employed in conjunction with the two of more sources. The detector may have a relatively small in-plane extent and may be a flat-panel detector in some implementations.

In accordance with one aspect of the present technique, a method is provided for imaging a field of view. The method includes rotating an X-ray source about a field of view. The X-ray source may comprise two or more, discrete emission points. At least two of the emission points are individually activated at view angles around the field of view. Each emission point, when activated, emits a respective stream of radiation through a respective portion of the field of view. A plurality of signals generated in response to the respective streams of radiation are acquired from a detector. The plurality of signals are processed to generate one or more images. Systems and computer programs that afford functionality of the type defined by these methods are also provided by the present technique.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
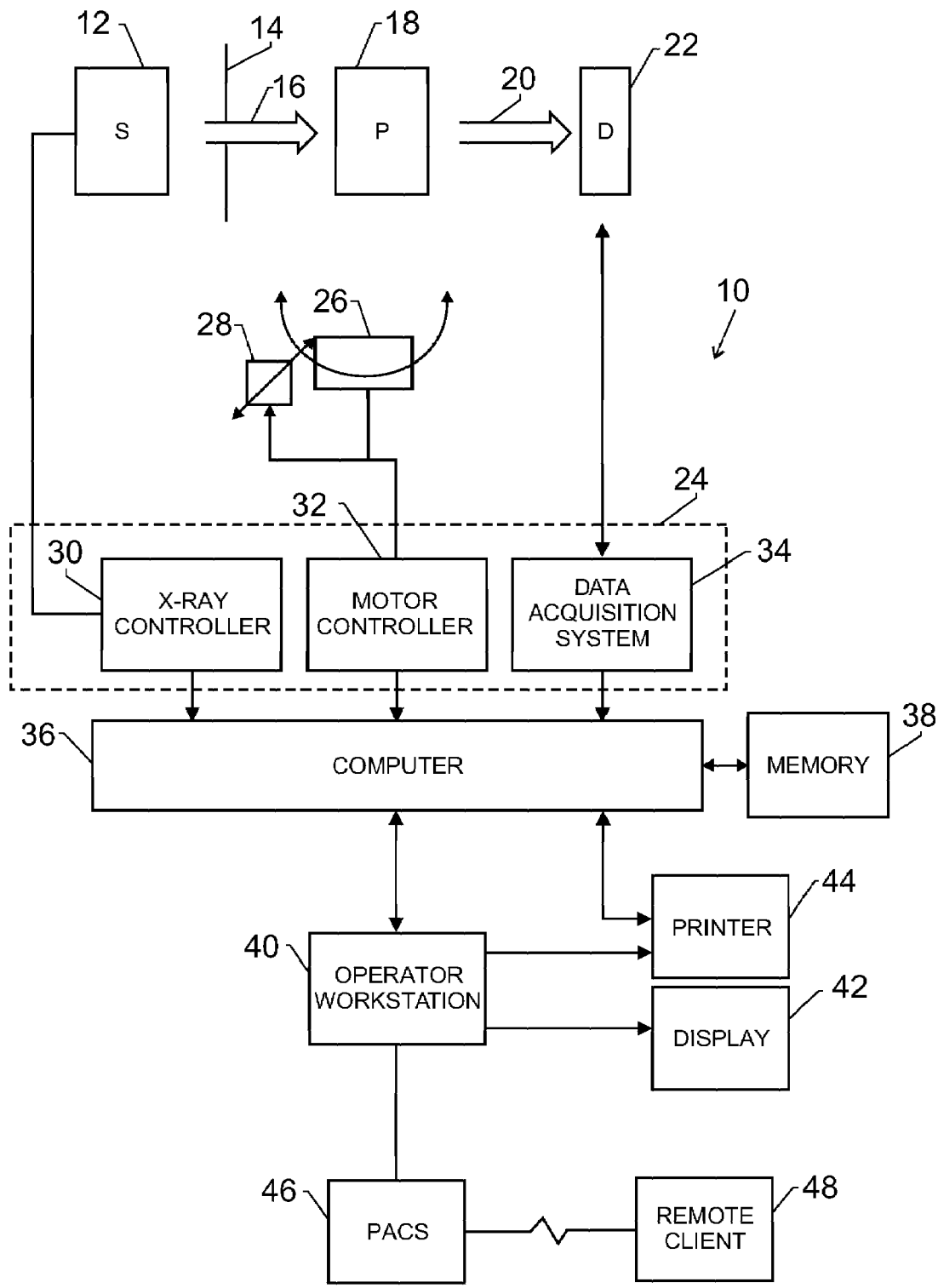
FIG. 1 is a diagrammatical view of an exemplary imaging system in the form of a CT imaging system for use in producing processed images, in accordance with one aspect of the present technique.

FIG. 1 illustrates diagrammatically an imaging system 10 for acquiring and processing image data. In the illustrated embodiment, system 10 is a computed tomography (CT) system designed to acquire X-ray projection data, to reconstruct the projection data into an image, and to process the image data for display and analysis in accordance with the present technique. Though the imaging system 10 is discussed in the context of medical imaging, the techniques and configurations discussed herein are applicable in other non-invasive CT imaging contexts, such as baggage or package screening.

In the embodiment illustrated in FIG. 1, CT imaging system 10 includes a source 12 of X-ray radiation. As discussed in detail herein, the source 12 of X-ray radiation may consist of two or more discrete, i.e., separated, emission points. For example, a conventional X-ray tube may be equated with a single emission point. Alternatively, an X-ray source such as a solid-state X-ray source having field emitters, or a thermionic X-ray source may include multiple emission points. Such solid-state or thermionic X-ray sources may be configured such that the respective emission points form an arc or a stationary ring.

Though the present description may discuss the rotation of an X-ray source 12, as may occur in conventional third-generation CT systems, one of ordinary skill in the art will appreciate that discussion of a rotating an X-ray source 12 also encompasses functional equivalents. For example, for a solid-state X-ray source 12 configured as a ring, the source 12 and respective emission points may not physically rotate. Instead, emission points along the ring may be activated in a sequential manner effectively equivalent to rotating an X-ray source 12. Therefore, where an X-ray source 12 or emission point is described as rotating, it is to be understood that such a rotation may result from the physical rotation of the source 12 or elements of source 12 or from such a functional equivalent.

The X-ray source 12 may be positioned proximate to a collimator 14. The collimator 14 may consist of a collimating region, such as lead or tungsten shutters, for each emission point of the source 12. The collimator 14 typically defines the size and shape of the one or more streams of radiation 16 that pass into a region in which a subject, such as a human patient 18, is positioned. A stream of radiation 16 may be generally cone-shaped, depending on the configuration of the detector array, discussed below, as well as the desired method of data acquisition. An attenuated portion of the radiation 20 passes through the subject, which provides the attenuation, and impacts a detector array, represented generally at reference numeral 22.

The detector 22 is generally formed by a plurality of detector elements, which detect the X-rays that pass through and adjacent to a subject of interest. The detector 22 may include multiple rows of detector elements. When such multi-row detectors are employed, the stream of radiation 16 will have a non-zero cone-angle associated with it for detector rows not in-plane with the active emission point. The following examples may make abstraction of this z-extent to simplify presentation, i.e., by limiting discussion to the detector elements in-plane with the active emission point. However, as one of ordinary skill in the art will appreciate, the following geometrical discussion and examples are equally applicable to multi-row detectors.

Each detector element, when impacted by an X-ray, produces an electrical signal that represents the intensity of the X-ray beam at the position of the element during the time the beam strikes the detector. Typically, signals are acquired at a variety of view angle positions around the subject of interest so that a plurality of radiographic views may be collected. These signals are acquired and processed to reconstruct an image of the features within the subject, as described below.

The X-ray source 12 is controlled by a system controller 24, which furnishes power, focal spot location, control signals and so forth for CT examination sequences. Moreover, the detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system 10 to execute examination protocols and to process acquired data. In the present context, system controller 24 also includes signal processing circuitry, typically based upon a general purpose or application-specific digital computer, and associated memory circuitry. The associated memory circuitry may store programs and routines executed by the computer, configuration parameters, image data, and so forth. For example, the associated memory circuitry may store programs or routines for implementing the present technique.

In the embodiment illustrated in FIG. 1, system controller 24 may control the movement of a rotational subsystem 26 and linear positioning subsystem 28 via a motor controller 32. In imaging system 10 in which the source 12 and/or the detector 22 may be rotated, the rotational subsystem 26 may rotate the X-ray source 12, the collimator 14, and/or the detector 22 through one or multiple turns around the patient 18. It should be noted that the rotational subsystem 26 might include a gantry. The linear positioning subsystem 28 enables the patient 18, or more specifically a patient table, to be displaced linearly. Thus, the patient table may be linearly moved within the gantry to generate images of particular areas of the patient 18.

As will be appreciated by those skilled in the art, the source 12 of radiation may be controlled by an X-ray controller 30 disposed within the system controller 24. The X-ray controller 30 may be configured to provide power and timing signals to the X-ray source 12. In addition, the X-ray controller may be configured to provide focal spot location, i.e., emission point activation, if the X-ray source 12 is a distributed source, such as a solid-state or thermionic X-ray source configured as an arc or ring.

Further, the system controller 24 may comprise a data acquisition system 34. In this exemplary embodiment, the detector 22 is coupled to the system controller 24, and more particularly to the data acquisition system 34. The data acquisition system 34 receives data collected by readout electronics of the detector 22. In particular, the data acquisition system 34 typically receives sampled analog signals from the detector 22 and converts the data to digital signals for subsequent processing by a computer 36.

The computer 36 is typically coupled to the system controller 24. The data collected by the data acquisition system 34 may be transmitted to the computer 36 for subsequent processing and reconstruction. For example, the data collected from the detector 22 may undergo pre-processing and calibration at the data acquisition system 34 and/or the computer 36 to condition the data to represent the line integrals of the attenuation coefficients of the scanned objects. The processed data, commonly called projections, may then be reordered, filtered, and backprojected to formulate an image of the scanned area. Once reconstructed, the image produced by the system of FIG. 1 reveals an internal region of interest of the patient 18 which may be used for diagnosis, evaluation, and so forth.

The computer 36 may comprise or communicate with a memory 38 that can store data processed by the computer 36 or data to be processed by the computer 36. It should be understood that any type of computer accessible memory device capable of storing the desired amount of data and/or code may be utilized by such an exemplary system 10. Moreover, the memory 38 may comprise one or more memory devices, such as magnetic or optical devices, of similar or different types, which may be local and/or remote to the system 10. The memory 38 may store data, processing parameters, and/or computer programs comprising one or more routines for performing the processes described herein.

The computer 36 may also be adapted to control features enabled by the system controller 24, i.e., scanning operations and data acquisition. Furthermore, the computer 36 may be configured to receive commands and scanning parameters from an operator via an operator workstation 40 which may be equipped with a keyboard and/or other input devices. An operator may thereby control the system 10 via the operator workstation 40. Thus, the operator may observe the reconstructed image and other data relevant to the system from computer 36, initiate imaging, and so forth.

A display 42 coupled to the operator workstation 40 may be utilized to observe the reconstructed image. Additionally, the scanned image may be printed by a printer 44 which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote system 48, radiology department information system (RIS), hospital information system (HIS) or to an internal or external network, so that others at different locations may gain access to the image data.

One or more operator workstations 40 may be linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

The CT imaging system 10 described above may be configured in a variety of ways to improve spatial and temporal resolution, to improve image quality, and/or to improve longitudinal coverage. Indeed, various source 12 and detector 22 configurations may be implemented which improve one or more of these parameters. For example, as discussed herein, an X-ray source 12 that employs multiple emission points may be employed. Activation of the emission points may be coordinated so that only one is active at a time, such as by employing an alternating activation scheme. In this manner, each emission point, when active, may provide a subset of the projection lines required to reconstruct an object within a given field of view. Combination of these subsets, however, allows the reconstruction of the field of view. In addition, because only a subset of the projection lines associated with the field of view are acquired at one time, the in-plane extent of the detector 22 may be reduced. Indeed, the in-plane extent of the detector 22 may be reduced to the degree that a flat-panel detector may be employed.

As one of ordinary skill in the art will appreciate, a variety of X-ray source 12 configurations and activation schemes may be practiced in accordance with the present technique. A number of exemplary configurations and schemes are discussed herein. It is to be understood, however, that the included examples do not limit the scope of the present technique. Instead, the present technique may broadly be understood to encompass any X-ray source configuration that allows for multiple, discrete emission points as well as any activation scheme for such emission points.

Figure 2:
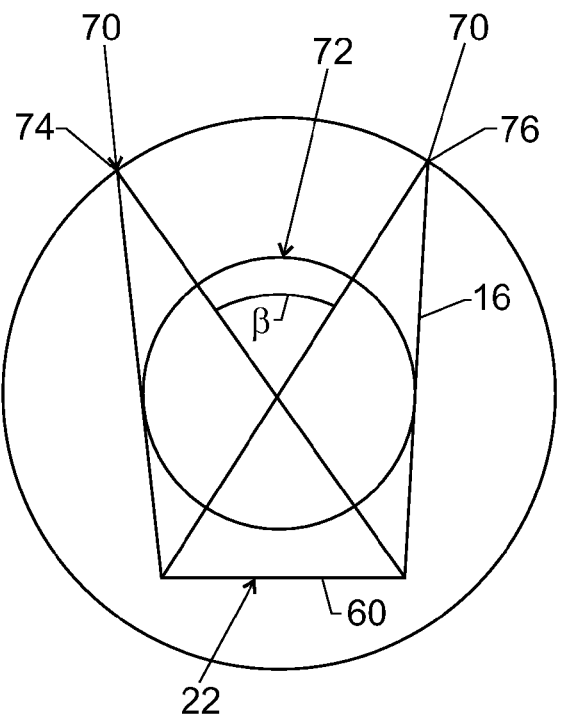
FIG. 2 is an in-plane view of a pair of X-ray emission points in a full field-of-view configuration, in accordance with the present technique.

For example, as depicted in FIG. 2, a pair of discrete emission points 70 offset in an azimuthal direction are depicted in an %-plane, as the source 12 of radiation. The emission points 70 may be configured to be the same perpendicular distance from the detector 22, such as flat-panel detector 60, or may be different distances. Each emission point 70 may be an X-ray tube, an emitter of a solid-state or thermionic X-ray source, or some other focal point from which X-rays may be emitted when activated. The X-ray source 12, and its respective emission points 70, may be gridded. The emission points 70 may also be offset in z, as discussed later in more detail.

The emission points 70 may be rotated about the desired field of view 72, allowing each emission point 70 to emit streams of radiation 16 from the desired view angles. As the emission points 70 rotate, they may be alternatingly activated such that only one emission point 70 emits X-rays at a given time. Each emission point 70 may be configured to emit a fan-shaped stream of radiation when activated, which circumscribes a portion of the field of view 72, such as half the field of view 72 as depicted in FIG. 2. The stream of radiation 16 passes through the field of view 72, and any attenuating matter within the field of view 72, before striking the detector 22, such as flat-panel detector 60. For each activation of an emission point 70, the data acquisition system 34 (FIG. 1) reads out the signals generated by the detector 22, which may be processed to generate the projection data. As the emission points 70 rotate about the field of view 72 the combined or aggregate acquired projection data describes the entire field of view.

For example, a first emission point 74, when active, may emit X-rays within a fan encompassing a portion of the field of view 72, such as half the field of view 72, as depicted in FIG. 2. Projection data may, therefore, be acquired for this portion by the detector 22, such as flat-panel detector 60, when the first emission point 74 is active. When the first emission point 74 is inactive, the second emission point 76 may be activated, allowing projection data to be acquired for a portion of the field of view 72 encompassed by the fan of X-rays emitted by second emission point 76. The emission points 70 may be rotated about the field of view 72, being alternatingly activated at each desired view angle, until the desired projection data has been acquired to reconstruct the field of view 72.

As will be appreciated by one of ordinary skill in the art, sufficient projection data to reconstruct the field of view 72 may be acquired with less than a full rotation of the emission points 70 about the field of view 72. Indeed, a half rotation plus the angle ($\beta$) between the two emission points 70, i.e., 180°+$\beta$, may be sufficient rotation to provide projection data to reconstruct the field of view 72.

Figure 3:
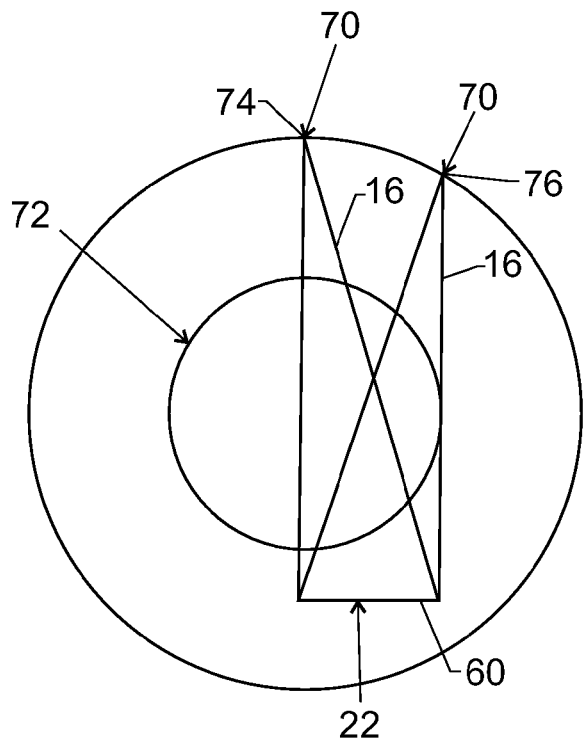
FIG. 3 is an in-plane view of a pair of X-ray emission points in a half field-of-view configuration, in accordance with the present technique.

Furthermore, the multiple emission points 70 may be configured so that their combined fans circumscribe only half, or some other portion, of the field of view 72 when active, i.e., a half field of view configuration. For example, referring to FIG. 3, two emission points 70 are depicted which, when active, emit X-rays within a fan encompassing only a portion of half of the field of view 72. The combined fans of the first and second emission points 74, 76, as depicted, circumscribe only half of the field of view 72. Limiting the fan angle, α, associated with each emission point 70, allows the in-plane extent of the detector 22, here flat-panel detector 60, to be further reduced since less of the field of view 72 is imaged when an emission point 70 is active. As one of ordinary skill in the art will recognize, sufficient projection data to reconstruct the field of view 72 using a half field of view configuration, as depicted in FIG. 3, may be acquired with a full rotation of the emission points 70 about the field of view 72.

In addition, it should be recognized that the X-ray emitted by the first emission point 74 and the second emission point 76 do not pass through the same regions of the field of view 72. In particular, the X-rays emitted by the first emission point 74 pass through the central region of the field of view 72, where the imaged object or patient is typically centered. Conversely, the X-rays emitted by the second emission point 76 pass through a peripheral region of the field of view 72, which may contain empty space or regions of the imaged patient or object that are of less interest. This relationship remains true as the first and second emission points 74, 76 rotate about the field of view 72, i.e., the first emission point 74 continues to image the central region of the field of view 72 while the second emission point 76 continues to image the periphery of the field of view 72.

Because of this distinction between the first and second emission points 74, 76, the first and second emission points 74, 76 need not be operated equivalently, such as when the periphery of the field of view 72 is of less or no interest. For example, fewer views may be acquired using the second emission point 76 if desired, i.e., the second emission point 76 may be activated less frequently than the first emission point 74. For instance, the second emission point 76 may be activated for every other view, or less, if desired. Similarly, the second emission point 76 may be operated for a reduced duration or duty cycle, or at a lower energy relative to the first emission point 74.

Likewise, the second emission point 76 may be of lower quality, i.e., lower flux, and so forth than the first emission point 74, if the peripheral region imaged by the second emission point 76 is less important. In particular, if lower attenuation, lower resolution, and/or higher noise are acceptable for the periphery of the region of interest 72, a lower flux second emission point 76 may be acceptable. Differential activation of the first and second emission points 74, 76 and/or the use of a lower flux second emission point 76 may allow different doses to be applied to the patient 18 at the center and periphery of the region of interest 72. In this manner, the dose received by the patient 18 may be customized based on the circumstances.

Figure 4:
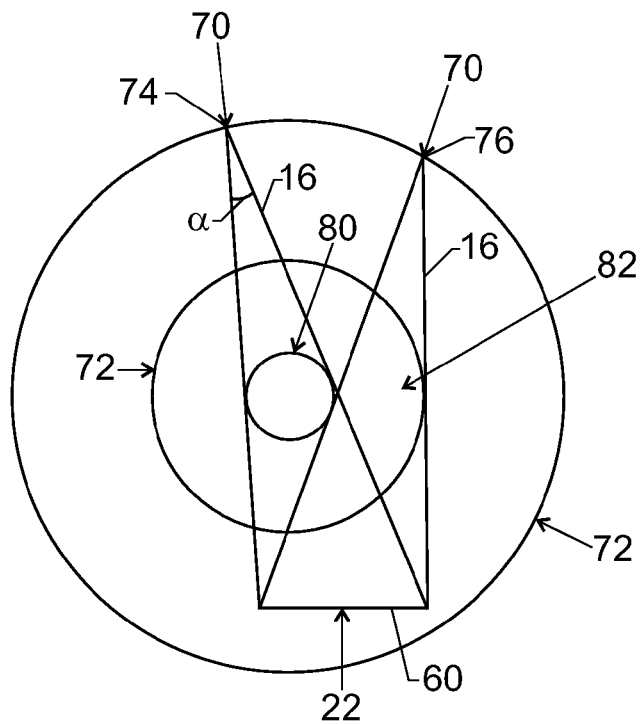
FIG. 4 is an in-plane view of a pair of X-ray emission points in an arbitrary field-of-view configuration, in accordance with the present technique.

These concepts may be extended to arbitrary configurations between a half and full field of view configuration or where a distinct central region of interest 80, such as a cardiac field of view, may be present. For example, as depicted in FIG. 4, the first and second emission points 74, 76, may each circumscribe the different portions of the field of view 72, i.e., the central region of interest 80 and the peripheral region 82 respectively. As one of ordinary skill in the art will appreciate, the discussion of the central region of interest 80 and peripheral region 82 with regard to FIG. 4 is analogous to and expands upon the related discussion with regard to FIG. 3.

In particular, referring to FIG. 4, the first emission point 74, when active, may emit X-rays within a fan encompassing the central region of interest 80 within the field of view 72. In this manner, the first emission point 74 may generate the projection lines associated with the central region of interest 80. The second emission point 76, when active, may emit X-rays within a fan encompassing a radial or peripheral portion 82 of the region of interest 72 outside the central region of interest 80. For example, one edge of the fan of X-rays emitted by the second emission point 76 may be tangential to the central region of interest 80 and the other edge may be tangential to the edge of the field of view 72. In this manner, the second emission point 76 may generate projection lines for a complementary portion of the field of view 72 not contained within the central region of interest 80.

As with the preceding examples, because the entire field of view 72 is not covered by a single emission point 70 and detector 22, the in-plane size of the detector 22 may be smaller than if a single emission point 70 were employed. For example, the detector 22 may have a relatively small in-plane extent and, indeed, may be substantially flat, such as flat panel detector 60. For example, for a radius of the central region of interest 80 of 15 cm and a radius of the field of view 72 of 50 cm, the detector 22 may be 30 percent or less of the size of a respective detector associated with the same field of view and a single emission point 70.

Half-scan data acquisition may be used to acquire data for reconstructing the central region of interest 80, i.e., 180°+α degrees of rotation. Further, because the fan angle, α, is less than when a single emission point 70 is employed, the half-scan may be performed more rapidly, thereby providing improved temporal resolution for imaging dynamic organs such as the heart. For example, α may equal 15° instead of 50° when a second emission point 76 is employed such that the half-scan data acquisition may encompass 195° of rotation of the first emission point 74 instead of 230° degrees of rotation. However, a full rotation, i.e., 360°, of the first and second emission points 74, 76 may be needed to acquire data for reconstructing the full field of view 72, i.e., to fully reconstruct the peripheral region 82.

As noted above with regard to the half field of view configuration of FIG. 3, fewer views using the second emission point 76 may be acquired if desired, such as when the peripheral views supplied by the second emission point 76 are less important. Similarly, the second emission point 76 may be activated less frequently than the first emission point 74 or for a reduced duration, as discussed in the preceding example. Likewise, as previously discussed, the second emission point 76 may be of lower quality, i.e., lower flux, and so forth than the first emission point 74, if the peripheral region 82 imaged by the second emission point 76 is less important.

Differential activation of the first and second emission points 74, 76 and/or the use of a lower flux second emission point 76 may allow different doses to be applied to the patient 18 inside and outside of the central region of interest 80. Indeed, in some instances, such as where the object or organ to be imaged is within the central region of interest 80, it may be possible to leave the second emission point 76 inactive during image data acquisition. In such an implementation, the data acquired corresponding to the peripheral region 82 will be incomplete, but may still be reconstructed using special reconstruction techniques if desired, such as if some portion of the imaged object lies within the peripheral region 82. In this manner, the dose received by the patient 18 may be customized based on the circumstances.

Though the preceding examples discuss implementations including two emission points 70, the technique is extendable to three or more emission points 70. For example, three or more X-ray tubes may be employed or a solid-state or thermionic X-ray source 12 may be employed which includes three or more addressable emission points 70 configured in an arc or ring. Other X-ray sources 12, which include discrete and addressable emission points 70, may also be suitable for use with the present techniques.

Figure 5:
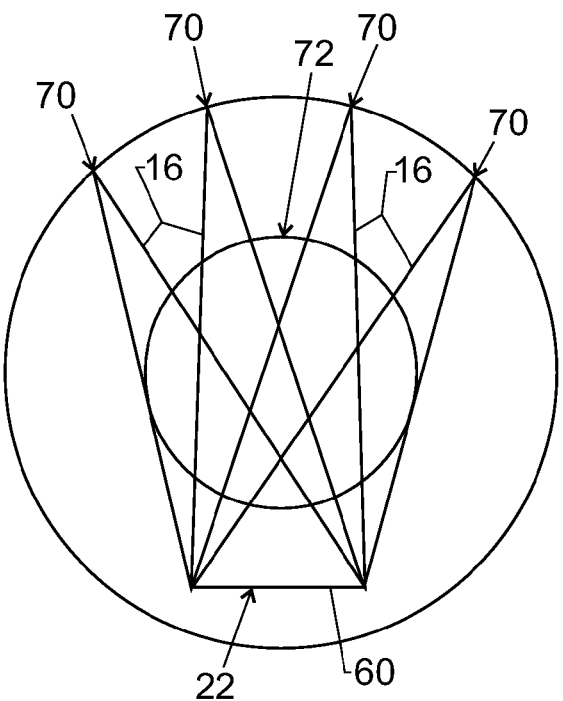
FIG. 5 is an in-plane view of four X-ray emission points in a full field-of-view configuration, in accordance with the present technique.

For example, FIG. 5 depicts four emission points 70 in a full field-of-view configuration, analogous to that depicted in FIG. 2. The emission points 70 may be configured to be the same perpendicular distance from the flat-panel detector 60 or may be different distances. As discussed with regard to FIG. 2, the emission points 70 may be rotated about the desired field of view 72 such that each emission point 70 may emit a stream of radiation 16 from the desired view angles.

As the emission points 70 rotate, they may be alternatingly activated such that only one emission point 70 emits X-rays at a given time. Each emission point 70 may be configured to emit a fan-shaped stream of radiation when activated, which circumscribes a portion of the field of view 72. The stream of radiation 16 passes through the field of view 72, and any attenuating matter within the field of view 72, before striking the flat-panel detector 60. For each activation of an emission point 70, the data acquisition system 34 (FIG. 1) reads out the signals generated by the detector 22, which may be processed to generate the projection data. As the emission points 70 rotate about the field of view 72 the combined or aggregate acquired projection data describes the entire field of view. As discussed above, in such a full field-of-view configuration, sufficient projection to reconstruct the field of view 72 may be acquired with a half-scan acquisition, i.e., 180°+ some additional angle depending on the geometry.

Similarly, a half field of view configuration may be implemented using more than two emission points 70. For example, referring to FIG. 6, four emission points 70 are depicted whose fan-shaped streams of radiation 16 generally circumscribe half, or some other portion, of the field of view 72. Each emission point 70 may be alternatingly activated, as described above, such that only one emission point 70 is active at a time. Due to the limited fan angle, α, associated with each emission point 70, the detector 22 may have a reduced in-plane extent. In such a half field of view configuration, sufficient projection data to reconstruct the field of view 72 may be acquired with a full rotation of the emission points 70 about the field of view 72.

Figure 6:
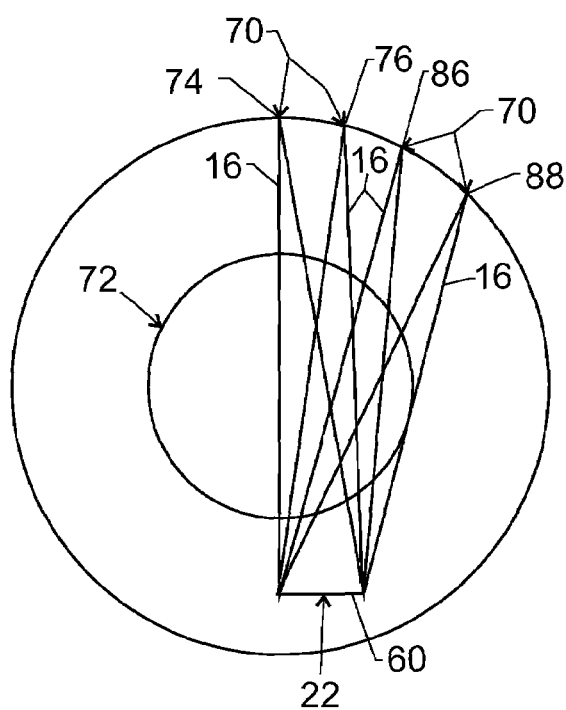
FIG. 6 is an in-plane view of four X-ray emission points in a half field-of-view configuration, in accordance with the present technique.

Furthermore, as noted above, the emission points circumscribe different radial regions of the field of view 72. For example, the first emission point 74 defines a central region while the second emission point 76 circumscribes the next outward radial region. Similarly, the third emission point 86 circumscribes the next radial region and the fourth emission point 88 circumscribes the peripheral or outer radial region. Because the emission points 70 circumscribe different radial regions of the field of view 72, different emission points 70 may remain inactive during an imaging sequence if the radial region they circumscribe is of no or little interest. For example, the fourth emission point 88 may remain inactive if the peripheral region of the field of view 72 contains empty space or is otherwise of no interest. As with the previous discussion of a half field of view configuration, sufficient projection data to reconstruct the field of view 72 using a half field of view configuration, as depicted in FIG. 6, may be acquired with a full rotation of the emission points 70 about the field of view 72.

Similarly, and as discussed with regard to FIGS. 3 and 4, the first, second, third, and fourth emission points 74, 76, 86, 88 need not be operated equivalently to the extent that the different radial regions they circumscribe are of different interest or importance. For example, each emission point 70 may be active for different numbers of views. For example, the first and second emission points 74, 76 may be active for every view, the third emission point 86 may be active for every other view, and the fourth emission point 88 may not be active for any view. Such an implementation might allow images to be constructed with good quality toward the center of the field of view, less quality outside of the center, and with no image of the peripheral region of the field of view 72 being generated. Similarly, different emission points, such as the fourth emission point 88, may be operated for a reduced duration or at a lower energy relative to the first emission point 74. Likewise, emission points 70 may vary in quality, i.e., flux, based on the radial region they circumscribe. For example, in an X-ray tube implementation, the third and/or fourth emission points 86, 88 may be low quality, i.e., low flux, X-ray tubes.

Therefore, as the number of X-ray emission points 70 increases, the ability to adapt the X-ray dose to the patient 18 or imaged object may also increase. In particular, possible number of radial regions increases as the number of emission points 70 increases. As the number of radial regions increases, the opportunities to employ differential operation, such as activations and/or durations, or different hardware configurations, such as low-flux X-ray tubes, also increases. In this manner, the dose received by the patient 18 and the image quality in different portions of the image may be customized based on the circumstances.

Figure 7:
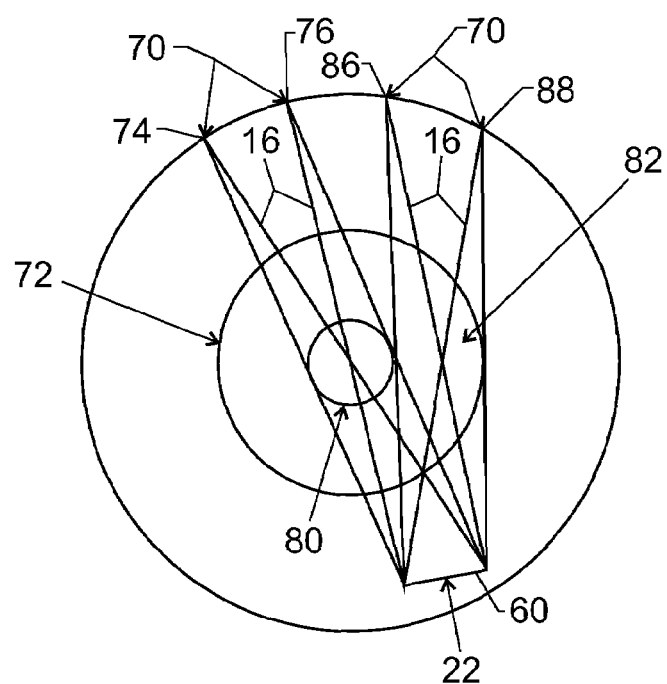
FIG. 7 is an in-plane view of four X-ray emission points in an arbitrary field-of-view configuration, in accordance with the present technique.

Likewise, the use of additional emission points 70 may be extended to arbitrary configurations or to configurations with a distinct central region of interest 80, such as a cardiac field of view 80, as discussed with regard to FIG. 4. For example, referring to FIG. 7, the first and second emission points 74, 76 may circumscribe the central region of interest 80 of the field of view 72. Conversely, the third and fourth emission points 86, 88 may circumscribe the peripheral region 82 of the field of view 72. The emission points 70 may be differentially operated or constituted, as discussed with regard to FIGS. 4 and 6, such that patient dosage may be adapted or adjusted based on circumstance. For example, the third and/or fourth emission points 86, 88 may not be activated or may be activated for only a subset of the possible view angles when the peripheral region 82 is of less or no interest. Similarly, if the peripheral region 82 is of less interest, the third and fourth emission points 86, 88 may be low quality, such as low flux, X-ray tubes or emitters.

As with the preceding examples, because the entire field of view 72 is not covered by a single emission point 70 and detector 22, the in-plane size of the detector 22, such as flat-panel detector 60, may be smaller than if a single emission point 70 were employed. Similarly, half-scan data acquisition using the first and second emission points 74, 76 may be used to acquire data for reconstructing the central region of interest 80, i.e., 180°+ some additional angle of rotation. However, a full rotation, i.e., 360°, of the first, second, third, and fourth emission points 74, 76, 86, 88 may be needed to acquire data for reconstructing the full field of view 72, i.e., to fully reconstruct the peripheral region 82.

While the preceding example depict configurations employing two or four emission points 70, one of ordinary skill in the art will appreciate that the disclosed techniques extend to other configurations in which more than one emission point 70 is present. Similarly, field of view configurations other than those depicted are not excluded from the present technique and may benefit from the use of multiple emission points 70, as discussed herein.

Figure 8:
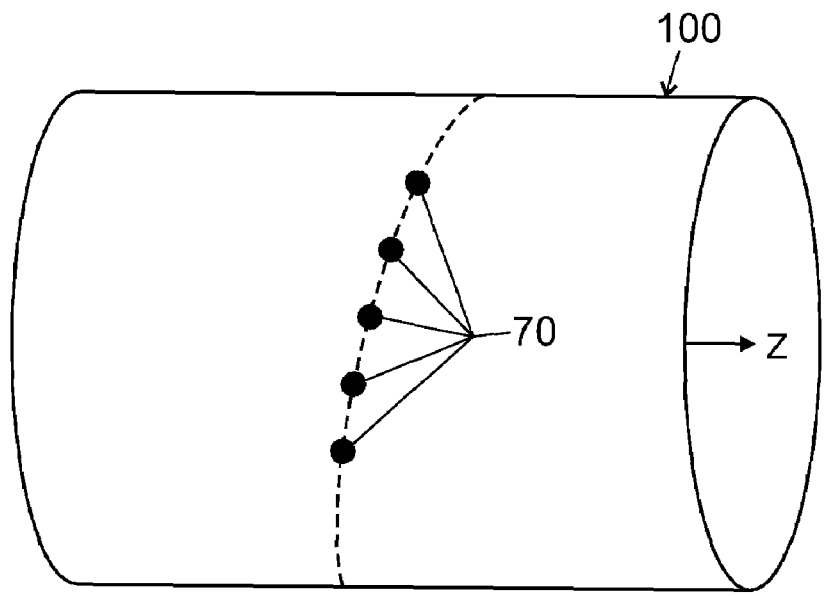
FIG. 8 is a perspective view of a CT scanner having a configuration of emission points that are offset along the longitudinal axis, in accordance with the present technique.

Furthermore, it may sometimes be desirable to offset the emission points 70 in the z-direction. For example, as shown in FIG. 8, a z-offset may be applied to consecutive emission points 70, resulting in a slightly tilted arc, relative to the primary axes of the CT scanner 100, of emission points 70.

This may be particularly useful for helical cone-beam acquisitions, because the resulting dataset may be reordered to emulate an acquisition obtained with a single emission point. To achieve such a result, the z-offsets, and therefore the pitch of the resulting arc, will depend on the helical pitch employed during image acquisition. The z-offsets may be adjusted to accommodate a desired helical pitch.

Figure 9:
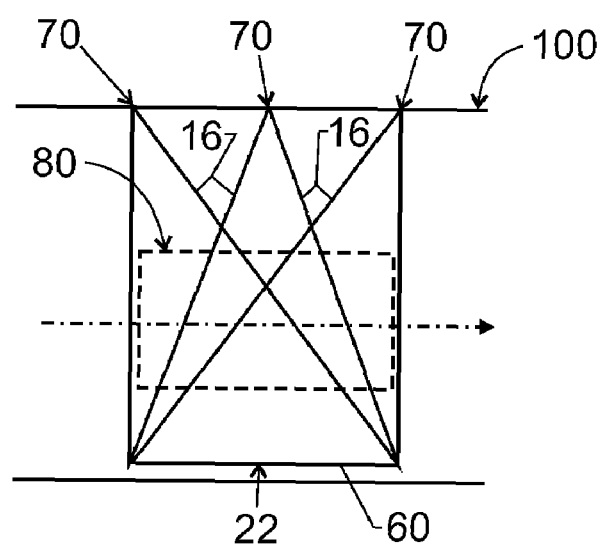
FIG. 9 is a side view of multiple axial X-ray emission points and a detector, in accordance with the present technique.

In addition, for cone-beam and volumetric CT geometries, it may be desirable to include additional emission points 70 along the longitudinal axis. In particular, the use of multiple emission points 70 along the longitudinal axis may allow the axial extent of the detector 22 to be reduced instead of or in addition to the reduction of the in-plane extent of the detector discussed above. For example, referring to FIG. 9, three emission points 70 deployed along the longitudinal axis of a CT scanner 100 are depicted. The emission points 70 may be fired alternatingly, such as sequentially, so that only one emission point 70 is active at a time. A detector 22, such as flat-panel detector 60, with a reduced axial extent may be employed in conjunction with the multiple longitudinal emission points in a manner analogous to that discussed in the preceding examples. As in the preceding examples, implementations of the present technique longitudinally allow for the use of smaller cone angles and therefore smaller detectors 22 longitudinally.

Figure 10:
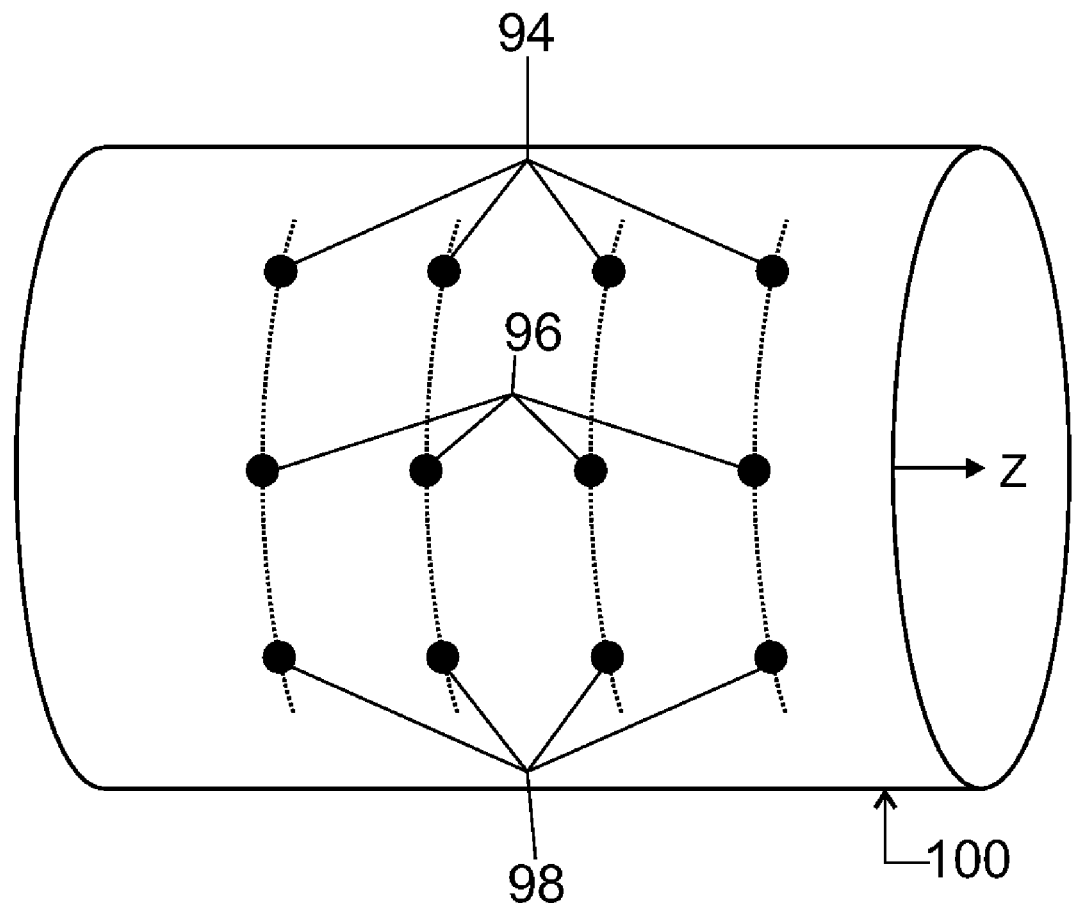
FIG. 10 is a perspective view of a CT scanner having a duplicate configuration of emission points along the longitudinal axis, in accordance with the present technique.

For example, referring to FIG. 10, three sets of duplicate emission points 94, 96, 98 are depicted along the longitudinal axis of a CT scanner 100. In the depicted example, each set of duplicate emission points 94, 96, 98 share coordinates within the y-plane, but differ in their position on the z-axis, i.e., longitudinally.

As described in the preceding in-plane offset and longitudinal offset examples, the techniques disclosed herein may provide a variety of benefits. For example, the reduced in-plane and/or longitudinal extent of the detector 22 may allow smaller, less expensive detectors, such as flat-panel detectors 60, to be employed (FIGS. 2-7 and 9). In general, it is easier and less expensive to manufacture a smaller detector, particularly a flat-panel detector.

In addition, the present techniques may provide greater spatial resolution, particularly away from the isocenter. In particular, a single emission point may be associated with a large fan angle and a correspondingly large detector. The focal spot associated with the emission point looks bigger at the edge of the detector due to an increase in the so-called apparent focal-spot size. The increased apparent focal-spot size may lead to inferior spatial resolution at the edges of the detector compared to the center of the detector. The reduced fan angles and smaller in-plane extent of detectors 22 used in conjunction with the present technique (FIGS. 2-7 and 9) may allow spatial resolution to be improved away from the iso-center, i.e., over the rest of the field of view, due to the smaller apparent focal size of the emission points 70.

Furthermore, the use of multiple emission points 70 (FIGS. 2-7) may allow for dynamic flux control during an image acquisition. For example, the multiple emission points 70 may be differentially activated based on view angle to maintain uniformity of the signal at the detector 22 and, thereby, improve efficiency and limit the dynamic range at the detector, or in order to optimize the dose or image quality. In particular, in medical imaging contexts, the patient 18 (FIG. 1) typically is elliptical in cross-section, resulting varying path lengths through the patient 18, i.e., the path length an X-ray traverses through the patient 18 varies depending on the view angle position relative to the patient 18. Conventional CT techniques may employ a bowtie filter, adapted to the general cross-section of the body region being imaged, to compensate for these varying path lengths.

The present techniques, however, allow for the real time flux modulation based on the anatomy of the patient 18, i.e., a virtual dynamic bowtie. In particular, at view angles corresponding to a short path length through the patient 18, such as through the chest and back, an emission point 70 may be activated to emit X-rays having lower flux. Conversely, at view angles corresponding to a long path length, such as from shoulder to shoulder, an emission point 70 may be activated to emit X-rays having higher flux. Similarly, for intermediate path lengths, the flux of the emitted X-rays may be suitably adjusted. Furthermore, the flux associated with a view angle position may be dynamically adjusted as a patient is linearly displaced through the CT scanner. In this manner, the effects of a bowtie filter may be replicated while allowing dynamic adjustment to maintain uniformity of signal at the detector 22.

The present techniques may also allow for the use of various detector technologies, such as energy discrimination detectors, so that CT techniques such as energy discrimination CT may be performed. Because of the smaller detector extent in the in-plane and/or longitudinal directions, such exotic technologies may more affordably be implemented. Similarly, such detectors may also be more easily manufactured to accommodate the reduced detector dimensions associated with the present techniques. In addition, the smaller fan angles and cone angles associated with the present technique reduce scatter in the X-ray intensity measurements and may allow the anti-scatter grid to be omitted from the detector, thereby increasing detector efficiency.

While the invention may be susceptible to various modifications and alternative forms, specific embodiments have been shown by way of example in the drawings and have been described in detail herein. However, it should be understood that the invention is not intended to be limited to the particular forms disclosed. For example, though imaging in a medical context has been discussed, the present techniques may also be applied in other imaging contexts, such as the screening of baggage, packages, and passengers. Rather, the invention is to cover all modifications, equivalents, and alternatives falling within the spirit and scope of the invention as defined by the following appended claims.

What is claimed is:

1. A CT system comprising:
    two or more X-ray sources radially offset from one another about an imaging volume and configured to rotate about the imaging volume, wherein each X-ray source comprises a separate and discrete emitter of electrons, and when activated, each X-ray source illuminates substantially different radial portions of the imaging volume;
    a controller configured to control operation of the two or more X-ray sources; and
    a detector configured to rotate about the imaging volume and to generate signals in response to emitted X-rays.

2. The CT system of claim 1, wherein each of the discrete emitters is one of a thermionic emitter, a field emitter, or a dispenser cathode.

3. The CT system of claim 1, wherein the controller is configured to control operation of the two or more X-ray sources such that the two or more X-ray sources differentially emit X-rays.

4. The CT system of claim 1, wherein the detector is a flat panel detector.

5. A CT system comprising:
    two or more radially offset emission points configured to rotate about an imaging volume, wherein each emission point, when active, emits X-rays in fan beams or cone beams that are substantially non-overlapping where they enter a field of view of the imaging volume;

a controller configured to control operation of the two or more emission points; and a detector configured to rotate about the imaging volume and to generate signals in response to the X-rays.

6. The CT system of claim 5, wherein the X-rays emitted by at least one offset emission point pass through the isocenter of the field of view and the X-ray emitted by at least one different offset emission point do not pass through the isocenter.

7. The CT system of claim 5, wherein two or more offset emission points comprise two offset emission points, three offset emission points, or four offset emission points.

8. The CT system of claim 5, wherein the controller is configured to differentially operate the two or more offset emission points.

9. The CT system of claim 5, wherein the detector is a flat panel detector.

10. A CT system comprising:
two or more emission points configured to rotate about a field of view and, when rotated, to each emit X-rays that pass through different radial regions of the field of view, wherein each of the two or more emission points comprises a separate and discrete emitter of electrons;

a controller configured to differentially operate the two or more emission points; and a detector configured to generate signals in response to the X-rays.

11. The CT system of claim 10, wherein the controller differentially operates the two or more emission points by operating at least one emission point at a different electric current or mA than another.

12. The CT system of claim 10, wherein the controller differentially operates the two or more emission points by activating at least one emission point for a greater duration than another.

13. The CT system of claim 10, wherein the controller differentially operates the two or more emission points by operating at least one emission point more frequently than another.

14. The CT system of claim 10, wherein the two or more emission points are associated with one or more X-ray tubes, one or more solid-state X-ray sources, or one or more thermionic X-ray sources.

15. A method comprising:
rotating two or more radially offset emission points about an imaging volume;

differentially emitting X-rays from the two or more emission points as the emission points rotate, such that a patient's dose is minimized; and generating signals in response to the incidence of the X-rays on a detector.

16. The method of claim 15, wherein differentially emitting X-ray comprises operating at least one emission point at a different flux than another.

17. The method of claim 15, wherein differentially emitting X-ray comprises activating at least one emission point for a greater duration than another.

18. The method of claim 15, wherein differentially emitting X-ray comprises operating at least one emission point more frequently than another.

* * * * *

UNITED STATES PATENT AND TRADEMARK OFFICE
CERTIFICATE OF CORRECTION

PATENT NO. : 7,639,775 B2 Page 1 of 1
APPLICATION NO. : 11/970403
DATED : December 29, 2009
INVENTOR(S) : DeMan et al.

It is certified that error appears in the above-identified patent and that said Letters Patent is hereby corrected as shown below:

In Column 6, Line 13, delete "%-plane," and insert -- xy-plane, --, therefor.

In Column 11, Line 30, delete "y-plane," and insert -- xy-plane, --, therefor.

Signed and Sealed this

Twenty-fifth Day of May, 2010

David J. Kappos
*Director of the United States Patent and Trademark Office*